United States Patent [19]
Brown et al.

[11] Patent Number: 4,582,798
[45] Date of Patent: Apr. 15, 1986

[54] PREPARATION AND USE OF ENZYME-DETERGENT EXTRACTED *STREPTOCOCCUS EQUI* VACCINE

[75] Inventors: Karen K. Brown, Kansas City, Mo.; Sharon A. Bryant, Shawnee; Kenneth S. Lewis, Olathe, both of Kans.

[73] Assignee: Miles Laboratories, Inc., Elkhart, Ind.

[21] Appl. No.: 674,449

[22] Filed: Nov. 23, 1984

[51] Int. Cl.$^4$ .................. C12P 21/00; C12N 1/20; A61K 39/09
[52] U.S. Cl. .................................. 435/68; 424/92; 424/88; 260/112 R; 435/253
[58] Field of Search ............... 435/68, 253; 424/92, 424/93; 260/112 R

[56] References Cited

U.S. PATENT DOCUMENTS 3,793,150  2/1974  Usdin ............................ 424/92
3,852,420 12/1974  Usdin ............................ 424/92

OTHER PUBLICATIONS

Woolcock, J. B., Infect. and Immun., 1974, pp. 116–122.
Srivastava, S. K. et al., Am. J. Vet. Res., vol. 44, pp. 41–45, 1983.
Srivastava, S. K. et al., Can. J. Comp. Med., vol. 46, pp. 51–56, 1982.
Erickson, E. D. et al., Can. J. Comp. Med., vol. 39, pp. 110–115, 1975.
Calandra, G., et al., Infection and Immunity, vol. 28, pp. 1033–1037, 1980.
De Cueninck, B., et al., Infection and Immunity, vol. 35, pp. 572–582, 1982.

*Primary Examiner*—Blondel Hazel
*Attorney, Agent, or Firm*—James A. Giblin

[57] ABSTRACT

Immunogenic protein material obtained from *Streptococcus equi* bacteria via enzymatic digestion and detergent treatment and useful as a vaccine.

5 Claims, No Drawings

PREPARATION AND USE OF ENZYME-DETERGENT EXTRACTED *STREPTOCOCCUS EQUI* VACCINE

RELATED APPLICATIONS

Patent applications Ser. No. 454,908, entitled Titration of Group C Streptococcal Antibody and Ser. No. 454,906 now U.S. Pat. No. 4,529,581, entitled Determining Potency of Streptococcal Preparations, both filed Dec. 30, 1982.

BACKGROUND OF THE INVENTION

1. Field

This disclosure is concerned with the preparation of an immunogenic protein material from *Streptococcus equi* bacteria using an enzymatic digestion and detergent treatment and use of the material as a vaccine against *Strep. equi* infection in equines.

2. Prior Art

*Streptococcus equi* is classified as a Lancefield Group C Streptococcus. See, for example, Bergey's Manual of Determinitive Bacteriology (8th Ed.), p. 498 (1974). It is recognized as the causative agent of a severe respiratory disease of horses referred to as "Strangles". The disease is endemic in most parts of the world and epidemic in the United States. Race and show horses are particularly susceptible to repeated infections due to the stress of travel and exposure to new contacts. The disease begins with a mucopurulent nasal discharge, temperatures of 103°–106° F., and severe inflammation of the upper respiratory mucosa. It finally progresses to lymphadenitis and abscess formation which is sometimes severe enough to restrict air intake and cause suffocation of the animal. Strangles results in extensive loss of condition (loss of weight) as it often runs a course of 4–6 weeks.

Because of the debilitating and in some cases lethal effects of *Strep. equi* infections in horses, attempts have been made over the years to prepare *Strep. equi* vaccines which could be used for active immunization purposes. Unfortunately, *Strep. equi* preparations have been noted for their affinity for dermal tissue, producing severe swelling and even abscess formation at the injection site. These known reactivities have tended to discourage the development and/or commercial use of immunizing *Strep. equi* products. Two commercially available Strangles vaccines do exist, however. The first commercial product was a whole culture, chemically inactivated *Strep. equi* preparation (supplied by Ft. Dodge Corporation). The second commercial product was a cell free M-protein vaccine (available from Burroughs Wellcome Co.) described as "a concentrated, aluminum hydroxide-absorbed suspension of purified antigens derived from *Strep. equi*". The method by which this vaccine is prepared is thought to be described in U.S. Pat. No. 3,793,150 and U.S. Pat. No. 3,852,420. The purification of such "M-like proteins" from *Strep. equi* is also described in an article by J. B. Woolcock, Infect. and Immun., July 1974, p. 116–122. As used herein, the expression "M-like protein" means the immunogenic protein(s) of the *Strep. equi* organism which appears similar in molecular weight and activity to the M-protein of group A streptococci.

The theory that a protein on the cell wall of the *Strep. equi* organism, referred to as an M-like protein, is the antigenic portion of the bacteria has been discussed in articles by S. K. Srivastava and D. A. Barnum in the Can. J. Comp. Med., Vol. 46, p. 51–56, 1982 and in the Am. J. Vet. Res., Vol. 44, p. 41–45, 1983 and in articles by E. D. Erickson and N. L. Norcross in the Can. J. Comp. Med., Vol. 39, p. 110–115, 1975. In all previous work, this M-like protein was extracted from the *Strep. equi* organism by subjecting the organism to low pH conditions (pH2) and high temperatures (95°–100° C.) for a given time (10–15 minutes). This has been referred to as a "heat extraction" method of preparing the M-like protein. The protein precipitates under these conditions and is solubilized by raising the pH of the solution to pH 7 or above.

We now have developed an improved method of removing the M-like protein from *Strep. equi* organisms, details of which are described herein.

We have now found that the antigenic M-like protein can be efficaciously removed from a *Strep. equi* culture in a two step process using lytic enzyme digestion followed by treatment with an anionic detergent and that this extract can be used to prepare a vaccine effective in immunizing horses against infection by *Strep. equi*. The potency of this antigen preparation has been determined using the method stated in above-cited patent application Ser. No. 454,906 now, U.S. Pat. No. 4,529,581, I entitled, Determining Potency of Streptococcal Preparations, and has been confirmed in a horse challenge study, described herein.

SUMMARY OF THE INVENTION

The procedure for our enzymatic extraction of Streptococcal M-like protein involves growth of a Streptococcal culture under growth-inducing conditions (e.g. at 37° C. in a suitable media) followed by concentration of the cells (e.g. by centrifugation or filtration). The cell concentrate is either diluted or washed in a suitable buffer. A bacteriolytic enzyme such as mutanolysin is then added to the cell concentrate and incubated at sufficient temperature and time for enzymatic lysis of part of the cell wall. Partial lysis means lysis sufficient to make the M-protein available for subsequent detergent extraction but without deleterious effect on the M-protein. In general, we found this can be accomplished by exposing the *Strep. equi* culture to the lytic enzyme at 37° C. for no more than about 24 hours at an enzyme concentration of about 1–10 units per ml of original culture volume. An anionic detergent such as sodium lauryl sulfate or dioctyl sodium sulfosuccinate is then added to the cell concentrate and allowed to incubate to complete the *Strep. equi* cell extraction treatment. Cells and cell debris are then removed by centrifugation or filtration and the final cell-free antigen solution sterilized by filtration or chemical treatment. The cell-free antigen solution is immunogenic and useful in immunizing horses against infection by *Strep. equi* organisms and has the following characteristics: a molecular weight ranging from 25,000 to 75,000 daltons; heat stability to about 95° C.; and trypsin sensitivity.

SPECIFIC EMBODIMENTS

The preferred bacteriolytic enzyme used in our method is mutanolysin (N-acetylmuramidase) which is obtained from the culture filtrate of *Streptomyces globisporus* and which is commercially available from Sigma Chemical Co., St. Louis, Mo. 63178 and Dainippon Pharmaceutical Co., Ltd., Osaka, Japan. Studies using mutanolysin as a method of lysing Streptococcal cell walls have been conducted for purposes other than M-like protein retrieval. Articles of these studies have been written by K. Yohagawa, et al in Antimicrobial Agents and Chemotherapy, August 1974, p. 156–165, G. B. Calandar and R. M. Cole in Infect. and Immun., June 1980, p. 1033–1037, and B. J. DeCueninck, et al., in Infect. and Immun., February 1982, p. 572–582. Mutanolysin and other bacteriolytic enzymes (glycosidases) such as egg white lysozyme are thought to act on linear sequences of N-acetylglucosamines and N-acetylmuramic acid residues of the bacterial cell walls.

EXAMPLE

1. *Strep. equi* deposited with American Type Culture Collection, Rockville, Md. 20852 as A.T.C.C. No. 39,506 was used. Grow *Strep. equi* in chemically defined medium (I. van de Rijn, Infect. and Immun., 27: 444–448, 1980) at 37° C. for 16 hours.
2. Concentrate *Strep. equi* cells to 10–50 fold using cross-flow filtration. Wash cells by addition of 0.1M Trizma—HCl buffer with pH adjusted to 6.5 with NaOH.
3. Concentrate washed *Strep. equi* cells to 20–100 fold using cross flow filtration.
4. Add mutanolysin as a 5,000 unit/ml solution to concentrated cells achieving a final enzyme concentration of 5 units per ml original culture volume. Incubate at 37° C. for 16 hours.
5. Add 10% sodium lauryl sulfate to achieve a final concentration of 0.05%. Incubate at 37° C. for 30 minutes.
6. Remove *Strep. equi* cells and cell debris by cross flow filtration or centrifugation.
7. Sterile filter effluent through 0.2 micron filter and hold at 4° C.

Antigen prepared according to the example was tested for potency via the previously-mentioned mouse combining power assay. In this assay, the antigenicity of the vaccine is measured by the increase in LD50 over the LD50 of the Antiserum Control. The greater this increase in LD50, the greater the antigenicity of the vaccine. Table 1 shows the results of vaccines tested via this assay. It should be noted that antigen diluted as much as 1:200 still demonstrates combining power.

TABLE 1

MOUSE COMBINING POWER RESULTS OF VACCINE PREPARATION

| Antigen Dilution Used To Prepare Vaccine | Mouse LD50 (Log) | LD50 Increase over Antiserum Control (Log) |
|---|---|---|
| 1:100 | 8.0 | 4.6 |
| 1:150 | 6.5 | 3.1 |
| 1:200 | 4.7 | 1.3 |
| Antiserum Control | 3.4 | — |
| Negative Control | 8.2 | — |

To prove that the enzyme-detergent treatment was the key factor contributing to antigen retrieval, the following experiment was conducted:

1. *Strep. equi* culture was grown and the cells were then harvested by centrifugation.
2. The cells were resuspended in buffer and aliquots of the suspension treated in the following manner: (In all cases, cells were removed following treatment by centrifugation and supernates filtered thru a 0.2 micron sterile filter.)

A. Suspension incubated at 50° C. for 16 hours, then 0.05% sodium lauryl sulfate (SLS) added and suspension held at 37° C. for 30 minutes.
B. Suspension incubated at 37° C. for 30 minutes after addition of 0.05% SLS.
C. Suspension incubated at 37° C. for 16 hours after addition of 0.05% SLS.
D. Suspension incubated at 50° C. for 16 hours after addition of 5 units/ml mutanolysin.
E. Suspension incubated at 50° C. for 16 hours after addition of 5 units/ml mutanolysin, followed by incubation at 37° C. for 30 minutes after addition of 0.05% SLS.
F. Suspension heated at 95° C. for 15 minutes after pH adjusted to 2.0. Suspension cooled and pH adjusted to 7.0.

Each of these preparations (A–F) were then tested in the mouse combining power assay to determine the amount of antigen released. The results (Table 2) show that detergent alone or in combination with heat (A, B, C) does not remove antigen. Mutanolysin incubated at 50° C. (D) removes minimal quantity of antigen compared with the combination of Mutanolysin and detergent (E). In fact, this latter technique (E) appears to remove antigen as well as the hot acid extraction (heat extraction) method (F) described in U.S. Pat. No. 3,793,150 and U.S. Pat. No. 3,852,420 based on combining power results shown in this table.

TABLE 2

MOUSE COMBINING POWER RESULTS OF ANTIGEN PREPARATION

| Treatment of Cells | Diln. of Preparation | Mouse LD50 (Log) | LD50 Increase over Antiserum Control (Log) |
|---|---|---|---|
| A. 16 hours at 50° C. + .05% SLS - 30 min. @ 37° C. | 1:5 | <5 | <1.4 |
| B. .05% SLS - 30 min @ 37° C. | 1:5 | <5 | <1.4 |
| C. .05% SLS - 16 hrs. at 37° C. | 1:5 | <5 | <1.4 |
| D. 5 units/ml mutanolysin 16 hrs. at 50° C. | 1:5 | 5.0 | 1.4 |
| | 1:10 | <5 | <1.4 |
| E. 5 units/ml mutanolysin 16 hrs. at 50° C. – .05% SLS - 30 min. at 37° C. | 1:5 | 7.4 | 3.8 |
| | 1:10 | 5.6 | 2.0 |
| F. pH 2–95° C. 15 minutes | 1:5 | 7.5 | 3.9 |
| | 1:10 | 5.5 | 1.9 |
| Antiserum Control | — | 3.6 | — |
| Negative Control | — | 7.7 | — |

Further work with the mutanolysin-detergent method has recently shown that antigen removal is even more effective at 37° C. than at 50° C. Therefore, the current process used to prepare the vaccines shown tested in Table 1 has been established at this preferred lower temperature of 37° C. To confirm the antigenicity of vaccines as measured in the mouse combining power assay, a vaccine efficacy study was conducted in equines using the vaccines shown in Table 1. Horses were given two doses of vaccine at 3 week intervals and then challenged with virulent *Strep. equi.* The efficacy of the vaccines was measured by the reduction in clinical symptoms observed post challenge. Clinical index values were assigned to Strangles symptoms for the purpose of efficacy evaluation. These clinical index values are shown in Table 3 and were assigned to each horse for each day symptoms were observed post challenge. Observations of the horses were made every other day for 49 days post challenge.

TABLE 3
CLINICAL INDEX VALUES ASSIGNED TO STRANGLES SYMPTOMS

| Symptom | Clinical Index Value |
| --- | --- |
| Abscess Formation | 20 points |
| White Blood Cell Count | |
| >50% increase | 5 points |
| >100% increase | 10 points |
| Temperature | |
| 102.0° F.–102.4° F. | 1 point |
| 102.5° F.–103.9° F. | 5 points |
| >104° F. | 10 points |
| Nasal Discharge | |
| Moderate | 5 points |
| Heavy | 10 points |

The results of the vaccine efficacy study are shown in Table 4 as the accumulation of clinical index values assessed during the 49 day observation period. The reduction of clinical indices is also shown in Table 4 as the percent reduction of the indices of the vaccine groups as compared to the nonvaccinated control group. These data suggest that efficacious vaccines can be produced using enzyme-detergent extraction of *Strep. equi.*

TABLE 4
Strep. Equi Efficacy Study Clinical Indices

| Clinical Symptom | Vaccine 1:100 | Vaccine 1:150 | Vaccine 1:200 | Non-Vaccinated Controls |
| --- | --- | --- | --- | --- |
| Total | | | | |
| Group Total | 819 | 1235 | 1586 | 2453 |
| Mean Value | 28.2 | 42.6 | 56.6 | 81.8 |
| % Reduction | 64% | 46% | 28% | — |
| Abscesses | | | | |
| Group Total | 180 | 420 | 680 | 1240 |
| Mean Value | 6.2 | 14.5 | 24.3 | 41.3 |
| % Reduction | 85% | 65% | 41% | — |
| WBC | | | | |
| Group Total | 375 | 470 | 585 | 820 |
| Mean Value | 12.9 | 16.2 | 20.9 | 27.3 |
| % Reduction | 53% | 41% | 23% | — |
| Temperature | | | | |
| Group Total | 179 | 230 | 211 | 222 |
| Mean Value | 6.2 | 7.9 | 7.5 | 7.4 |
| % Reduction | 16% | 0% | 0% | — |
| Nasal Discharge | | | | |
| Group Total | 85 | 115 | 110 | 70 |
| Mean Value | 2.9 | 4.0 | 3.9 | 2.3 |
| % Reduction | 0% | 0% | 0% | — |

Given the above disclosure, it is thought variations will occur to those skilled in the art. Accordingly, it is intended that the above specific Example should be construed as illustrative of the best mode to date of the invention disclosed and that the inventions disclosed should be limited only by the following claims.

We claim:

1. A method of preparing a cell-free antigenic solution useful in immunizing horses against *Streptococcus equi* bacteria, the method comprising the steps of:
   (a) growing *Streptococcus equi* bacteria under growth inducing conditions;
   (b) exposing the bacteria of step (a) to mutanolysin enzyme under conditions sufficient to partially lyse the cell wall;
   (c) exposing the partially lysed product of step (b) to an anionic detergent under conditions sufficient to extract immunogenic M-like protein(s) into a supernate;
   (d) separating the soluble extracted M-like protein supernate from bacterial cells and cell debris;
   (e) filter sterilizing the soluble M-like protein supernate product of step (d).

2. The method of claim 1 wherein the enzyme exposure of step (b) is at 37° C. for not more than about 24 hours at an enzyme concentration of 1–10 units per ml of original culture volume.

3. The method of claim 1 wherein the detergent of step (c) is sodium lauryl sulfate and the exposure is at 37° C. for not more than about 60 minutes at a detergent concentration of 0.01–0.10%.

4. The method of claim 1 wherein the sterilization of step (e) is by filtration through a 0.2 micron filter.

5. The method of claim 1 wherein the enzyme of step (b) is mutanolysin, the detergent of step (c) is sodium lauryl sulfate, and the sterilization of step (e) is by filtration through a 0.2 micron filter.

* * * * *